(12) United States Patent
Gaskin

(10) Patent No.: US 7,563,307 B2
(45) Date of Patent: Jul. 21, 2009

(54) COMBINED USE OF EXTERNAL AND INTERNAL SOLVENTS IN PROCESSING GASES CONTAINING LIGHT, MEDIUM AND HEAVY COMPONENTS

(75) Inventor: Thomas K. Gaskin, Spring, TX (US)

(73) Assignee: Advanced Extraction Technologies, Inc., Houston, TX (US)

(*) Notice: Subject to any disclaimer, the term of this patent is extended or adjusted under 35 U.S.C. 154(b) by 580 days.

(21) Appl. No.: 11/211,145

(22) Filed: Aug. 23, 2005

(65) Prior Publication Data

US 2006/0043000 A1   Mar. 2, 2006

Related U.S. Application Data

(60) Provisional application No. 60/603,933, filed on Aug. 24, 2004.

(51) Int. Cl.
*B01D 53/14* (2006.01)

(52) U.S. Cl. .................. 95/177; 95/230; 95/232; 95/235; 95/236

(58) Field of Classification Search .......... 95/177, 95/187, 192, 230, 232, 235, 236; 208/177; 423/655, 657, 658, 650
See application file for complete search history.

(56) References Cited

U.S. PATENT DOCUMENTS

| | | | | |
|---|---|---|---|---|
| 2,107,955 | A | * | 2/1938 | Nutter et al. ............... 137/207 |
| 2,685,941 | A | | 8/1954 | Kassel |
| 2,744,394 | A | | 5/1956 | Newton ................ 62/175.5 |
| 2,959,540 | A | | 11/1960 | Cahn et al. |
| 3,011,589 | A | * | 12/1961 | Meyer ...................... 95/41 |
| 3,026,682 | A | | 3/1962 | Palazzo et al. |
| 3,033,780 | A | * | 5/1962 | McGrath et al. .......... 208/136 |
| 3,062,015 | A | * | 11/1962 | Cost ........................ 62/635 |
| 3,102,012 | A | * | 8/1963 | Dowd ........................ 95/42 |
| 3,254,712 | A | * | 6/1966 | Sharp ....................... 166/266 |
| 4,035,167 | A | | 7/1977 | Starks ........................ 55/57 |
| 4,126,668 | A | * | 11/1978 | Erickson .................. 423/657 |
| 4,172,711 | A | * | 10/1979 | Bailey ...................... 62/619 |
| 4,623,371 | A | | 11/1986 | Mehra ....................... 62/17 |

(Continued)

FOREIGN PATENT DOCUMENTS

GB   2 331 526   5/1999

(Continued)

OTHER PUBLICATIONS

"Mehra Process Flexibility Improves gas Processing Margins", Yuv R. Mehra, Proceedings of the Sixty-Sixth GPA Annual Convention, Mar. 16-18, 1987.*

*Primary Examiner*—Duane Smith
*Assistant Examiner*—Ives Wu
(74) *Attorney, Agent, or Firm*—Howrey LLP

(57) ABSTRACT

A process for separating the components of a multi-component gas stream is disclosed. The multi-component gas stream is contacted with a solvent in an extractor to produce an overhead stream enriched with unabsorbed component(s) and a rich solvent bottoms stream enriched with absorbed component(s). The rich solvent bottoms stream is then flashed at reduced pressure to regenerate lean solvent and to recover the absorbed component(s) as an overhead stream. The regenerated solvent is recycled to the extractor. A portion of the circulating solvent comprises external solvent added to the system. A second portion of the circulating solvent comprises internal solvent contained in the feed gas.

32 Claims, 7 Drawing Sheets

U.S. PATENT DOCUMENTS

| | | | |
|---|---|---|---|
| 4,680,042 A | 7/1987 | Mehra | |
| 4,832,718 A | 5/1989 | Mehra | 62/17 |
| 4,883,514 A | 11/1989 | Mehra | 62/17 |
| 5,061,465 A * | 10/1991 | Carter | 423/229 |
| 5,220,097 A | 6/1993 | Lam et al. | 585/809 |
| 5,462,583 A * | 10/1995 | Wood et al. | 95/192 |
| 5,551,972 A | 9/1996 | Wood et al. | 95/192 |
| 6,698,237 B2 | 3/2004 | Gaskin | 62/632 |
| 2003/0106334 A1 | 6/2003 | Gaskin | |
| 2006/0146923 A1 * | 7/2006 | Mardinian | 375/222 |

FOREIGN PATENT DOCUMENTS

WO    WO 2005/090887    9/2005

* cited by examiner

COMBINED USE OF EXTERNAL AND INTERNAL SOLVENTS IN PROCESSING GASES CONTAINING LIGHT, MEDIUM AND HEAVY COMPONENTS

This application claims benefit of priority to U.S. provisional application Ser. No. 60/603,933 filed Aug. 24, 2004, the entire contents of which are incorporated by reference herein.

FIELD OF THE INVENTION

The invention relates to the field of chemical processing and, more specifically, to the processing of hydrocarbon gas streams. In particular, a method and apparatus for separating the components of a hydrocarbon gas stream is disclosed.

BACKGROUND OF THE INVENTION

Many hydrocarbon gases such as natural gas, cracked gas, or refinery off gas contain one or more light components that either contaminate the main gas or that are themselves valuable if they can be separated from the main gas stream. Such light gases include nitrogen, helium, and hydrogen. A number of economic considerations make it desirable to separate these light gases from a hydrocarbon gas stream.

For example, contamination of natural gas with one or more light components is particularly common. Natural gas is a mixture of hydrocarbons, including methane ethane, propane, butane and pentane. Natural gas can also contain nitrogen, helium, and acid gases such as carbon dioxide and hydrogen sulfide. Nitrogen is sometimes a natural component or may derive from nitrogen injections utilized for reviving oil wells in suitable formations. Helium occurs naturally in a small portion of natural gas reservoirs. Natural gas must meet certain criteria for acid gas content, heating value, dew point, and total inert content before the natural gas can be transported and marketed. Nitrogen content is often limited to less than 2-4% molar. Nitrogen must therefore be removed from natural gas containing more than the specified amount or the natural gas cannot be transported and marketed.

Natural gas is also produced in association with crude oil production as associated gas. This associated gas may contain naturally occurring nitrogen or may contain injected nitrogen used to enhance oil recovery. Associated gas must meet the same criteria as natural gas if the associated gas is to be transported and marketed.

Refinery and chemical plant streams often contain a number of light components such as nitrogen and hydrogen. Hydrogen is commonly contained in gas streams in refinery units. Hydrogen is added to some refinery operations and is produced as a side-product in other refinery unit operations. It is often desirable to separate this hydrogen from the refinery off gas because removed and recovered hydrogen can be recycled within the facility or sold, typically for a higher value than the heating value of the hydrogen in a refinery or chemical plant hydrocarbon stream. Likewise, removing nitrogen from the plant stream increases the heating value of the remaining hydrocarbon stream and potentially increases the stream's value as a fuel stream.

Separation of light components such as hydrogen or nitrogen from heavier components such as methane and ethane can increase the value of either or both of the resulting separate streams. Existing technologies for performing such separations include the use of selective membranes, adsorption systems such a pressure swing adsorption, and systems that utilize very low temperatures (cryogenic plants) such as expander, Joule-Thompson, or cascaded refrigeration plants.

Absorption using a physical solvent to remove the heavier components and therefore separate them from the light components, a process known as the Mehra Process™, can be employed. The Mehra Process is described in several U.S. patents, including U.S. Pat. Nos. 4,623,371, 4,832,718, 4,833,514, and 5,551,972, which are hereby incorporated herein by reference. These patents describe systems for absorption/flash regeneration systems for removal of light components such as nitrogen or hydrogen from heavier components such as methane or ethylene. They address systems wherein the physical solvent used is external, meaning a made up of component(s) added to the system, and also systems wherein the physical solvent used is internally generated and is therefore composed of heavier component(s) in the feed gas. An improvement to these processes is also described in U.S. Pat. No. 6,698,237B2 by Thomas K. Gaskin, which addresses use of stripping gas to enhance the performance of flash regeneration systems. A further improvement is described in U.S. patent application Ser. No. 11/076,356 (incorporated herein by reference) by Thomas K. Gaskin, which describes the use of cryogenic temperatures in processing gases in solvent absorption systems.

In the processes described in the above paragraphs, the heavier components are absorbed away from the light component(s) using a circulating physical solvent. Reducing the pressure of the rich solvent in a flash separator releases the heavier component and regenerates the solvent for recirculation to the absorber. The physical solvent may be a liquid chosen for its physical properties, one property being that it is heavier than the component to be absorbed from the light component. The physical solvent may also be made up entirely of the heaviest components of the feed gas stream. These heaviest components are those that do not readily vaporize in the flash regeneration of the circulating solvent. These absorption processes are characterized in that a feed stream comprising multiple components enters the process and two or more streams, each being enriched in at least one of the components, leaves the process. Any improvement to the process that results in, 1) increased process efficiency, or 2) reduced process implementation cost, or 3) improved operability, or 4) increased the purity of one or more of the exiting streams will be appreciated as a technical contribution to the art.

BRIEF SUMMARY OF THE INVENTION

One aspect of the present invention is a process for separating the components of a multi-component gas stream. The process comprises contacting the gas stream with a solvent in an extractor to produce an overhead stream that is enriched in at least one of the components and a solvent bottoms stream that is enriched in at least one of the other components. The enriched solvent bottoms stream is then flashed in at least one reduced pressure stage to release the absorbed component(s) from the solvent, thereby regenerating the lean solvent and providing the released component(s) as an overhead gas stream. The released component(s) stream may be compressed to produce a product stream. According to the present invention, a portion of the circulating solvent stream is made up of heavier components contained in the feed gas and another portion of the solvent is made up of external component(s) added to the system.

Utilizing an external solvent for a portion of the circulating solvent in applications where internal solvent can be used alone is counterintuitive, however use of some external solvent can at times reduce the number of pieces of equipment required to maintain inventory of solvent, reduce the utility requirements of the facility, and/or add favorable absorption selectivity to the circulating solvent. In applications where use of an internal solvent arrangement is not possible due to low availability of heavy solvent components in the feed gas, addition of some external solvent can allow a portion of the circulating solvent to be made up of internal components, thereby reducing the external solvent make-up requirements and/or utility and equipment requirements of the facility. Equipment cost and size can be further reduced by improved process instrumentation/control points chosen which allows reduction of the flash separator size. Purity of the produced product streams can be improved by either adding additional processing steps after the initial absorption/flash regeneration process, or by adjusting the inventory, characteristics, or operating conditions of the solvent.

DESCRIPTION OF PREFERRED EMBODIMENTS

Figure 1:
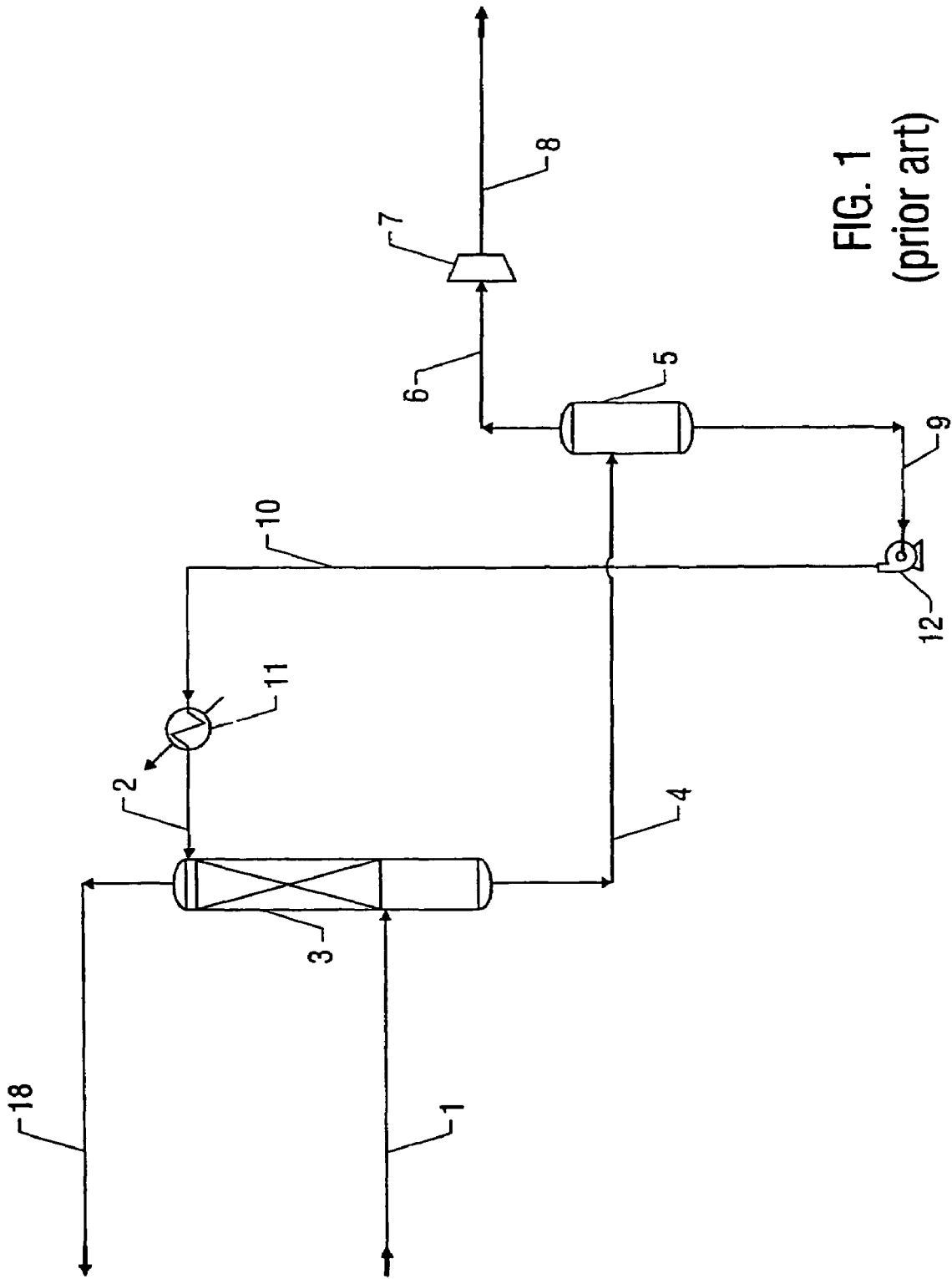
FIG. 1 shows a prior art process for separating the components of a gas stream.

It should be understood that pipelines are in fact being designated when streams are identified hereinafter and that streams are intended, if not stated, when materials are mentioned. Moreover, flow control valves, temperature regulator devices, pumps, compressors, and the like are understood as installed and operating in conventional relationships to the major items of equipment which are shown in the drawings and discussed hereinafter with reference to the continuously operating process of this invention. All of these valves, devices, pumps, and compressors, as well as heat exchangers, accumulators, condensers and the like, are included in the term "auxiliary equipment". The term, "absorber," is conventionally employed for a gas/solvent absorbing apparatus, but when utilized in the process of this invention with a physical solvent, it is considered to be an "extractor." However, the terms extractor and absorber may be used interchangeably in this document. As used herein, "extractor" refers to any apparatus known in the art in which a gas is contacted with a solvent to absorb part of the gas into the solvent. According to certain embodiments, the extractor may include internals such as plates, packing, baffles and the like, to promote mass transfer. As used herein, referring to a process step as producing a stream that is enriched in a certain component or components means that the fractional percentage of that component or components in the produced stream, relative to the other components, is greater than the relative percentage of that component or components in the stream entering the process step.

One aspect of the present invention is a process for separating the components of a multi-component gas stream. The process comprises contacting the gas stream with a solvent to produce an overhead stream that is enriched in at least one of the components and a rich solvent bottoms stream that is enriched in at least one of the other components. This contacting step is typically performed in an extractor. Typically the solvent absorbs the heavier component(s) of the multi-component stream, leaving the lighter component(s) as the overhead stream. The enriched solvent bottoms stream is flashed in at least one reduced pressure stage to release the absorbed component(s), thereby regenerating the solvent and providing the absorbed component(s) as an overhead stream. The regenerated solvent is recycled to the extractor.

It has been recognized that although the absorbed/released component(s) are typically the heavier component(s), often some amount of the light components co-absorb into the solvent and are therefore also released during the flash stage. This contamination of the heavier gas stream by the lighter component(s) is typically undesirable. One solution to this contamination has been to subject the enriched solvent to multiple flash stages and to recycle a portion of the gas released from one or more of the early flash stages back to the extractor. As explained further below, the gas from the early flash stage(s) is typically more contaminated with lighter components than is the gas released from the later flash stage(s). This recycle step has the effect of removing the lighter component from the product stream because the lighter component is recycled back to the extractor.

It is recognized that when the feed gas contains no components heavier than the primary heavy (absorbed) component of the feed gas, use of external solvent is required. A natural gas feed containing only nitrogen (light component) and methane (heavy component), requires use of external solvent. The external solvent may be chosen for ability to selectively absorb the desired heavy component. It is also desirable for the external solvent to be a heavy enough component, with a low vapor pressure, such that losses of the solvent through vaporization into product streams is minimized, thereby minimizing the amount of solvent addition required and minimizing contamination of the produced products.

It is recognized that when the feed gas contains a very significant amount of components heavier than the heavy (absorbed) component, an internally generated solvent may be used. If a natural gas streams contains nitrogen, methane, and significant components heavier than methane, up to and including butane or hexane and heavier, then external solvent is not required, and the solvent can consist of these heavier components. In this case, the light component is nitrogen, the methane is an intermediate weight component, and the butane, hexane and heavier components are referred to as heavy components. The nitrogen is the light, unabsorbed product stream. The methane is the absorbed in the extractor, and then released in the flash step as the heavier product gas, but now an intermediate weight product. Excess solvent, primarily butane, hexane and heavier components may be generated and withdrawn as a separate liquid product, the heaviest components of the feed gas stream. When the amount of these heavier components is not too large, additional equipment can be utilized to minimize the amount of solvent components lost to intermediate product stream, thereby continuing the ability to use internal solvent. Use of a chiller to recover solvent range heavy components from the intermediate component product stream would be typical. Those skilled in the art will recognize that a combination of the amount of heavy components in the feed gas, the vapor pressure of these components, and the level of solvent recovery employed together determine if the system can operate with internally generated solvent.

Characteristics of the solvent used affect the circulation rate required to achieve a desired separation of feed components. Heavier components with a higher molecular weight typically have fewer, larger molecules per unit volume. Those skilled in the art will recognize that use of heavier solvents will increase the circulation requirement, will increase the power required for the circulation, will increase any cooling duty required to meet a desired solvent temperature, and will increase the size of associated equipment.

The present invention utilizes a portion of external solvent that allows the second portion of the circulating solvent to be internally generated. According to one aspect of the present invention, introduction of the external solvent with a low vapor pressure dilutes the mole percent of the heavy internal solvent components in the bulk solvent stream to the extent that a portion of the solvent can be made up of internally generated solvent. According to another aspect of the present invention, the addition of the external portion of the solvent allows a portion of the bulk circulating solvent to be made up of internally generated solvent without the use of solvent recovery methods such as chilling the intermediate weight product stream for solvent recovery. It is counterintuitive that that a process that can at times be designed without use of an external solvent can in some cases require less equipment and/or energy usage by introduction of a an external solvent.

According to another aspect of the present invention, the use of the combined external/internal solvent also reduces the mole percent of external solvent when compared to an external solvent only system, thereby reducing the vapor pressure of the external solvent components by dilution with internal solvent. In this manner, the vaporization losses of external solvent into the product streams are reduced, and in some cases can be reduced to essentially no further addition. It is counterintuitive that by adding an external solvent to a system, it is at times possible that continued addition over time to the system is almost not required. Alternatively, a lighter, more efficient external solvent could be used, with losses of solvent only being equal to those lost when an external solvent only system is used.

The process of the present invention is generally applicable to any multi-component gas stream containing at least three components, wherein the different components of the gas stream have different solubilities in a hydrocarbon solvent and the heaviest component(s) are suitable as a portion solvent. The multi-component gas stream will typically comprise one or more hydrocarbons. When the process is operated at a reduced temperature utilizing a refrigerant such as propane or freon to achieve the reduced temperature, an operating temperature for the lean solvent in the range of +20° F. (−6.7° C.) to −40° F. (−40° C.) is typical. When the process is operated as a cryogenic process (such as described in patent application Ser. No. 11/076,356) by utilizing feed gas pressure reduction utilizing an expander or valve, or a combination of feed gas liquefaction followed by expansion, the lean solvent may operate at temperatures as low as −185° F. (−121° C.).

The external solvent that is added to the process can be of any type. Exemplary solvents include paraffinic solvents, naphthenic solvents, iso-paraffinic solvents, aromatic solvents, or specially blended solvents. According to one embodiment, the multi-component gas stream is countercurrently contacted with the solvent in the extractor. According to one embodiment, the feed gas and/or circulating solvent is cooled using a refrigerant stream. According to another embodiment the solvent is cooled using heat exchange with another process stream.

In another embodiment, the instrumentation used to control liquid solvent level in the flash regeneration vessels is designed to enable use of smaller vessels. This embodiment achieves improved process control by changing the surge point in the solvent system. According to one aspect of the present invention, the surge point for solvent volume in the system is made to be the center of the series of vessels as counted from and including the absorber through the lowest pressure flash. According to another aspect of the present invention, the control system utilizes the typical process measurement and control points to achieve improved process control with the re-assignment of the surge point by re-assigning which measurement point is adjusted by which control device (control valve). According to another aspect of the present invention, additional flow measurement points are added to provide feed-forward of process changes to calculating and control devices. It is not obvious that when a solvent is continuously circulated through a series of vessels containing a liquid level that which vessels have controlled levels and which single vessel is allowed to act as surge is important to stability of the control design.

The process of these embodiments is generally applicable to any solvent absorption/flash regeneration system for separating a multi-component gas stream containing at least two components(s).

These embodiments of improved process control can improve the absorption/flash regeneration process design by allowing vessels to be designed with lower surge times of liquid when such surge times were previously set by volumes required to maintain control. Improved control of the facility allows for less surge time to maintain control, and therefore smaller vessels may be allowed, and lower costs for construction of said vessels.

It is recognized that contaminants found in natural gas and refinery streams can include carbon dioxide, hydrogen sulfide, mercaptans, water, oxygen, carbon monoxide and others. Facilities are often required for removal of these components from either natural gas or from refinery streams. When a contaminant is removed, there is the potential for periods of time when the removal process does not perform as well as intended, and the some of the contaminant is not removed from the gas stream.

It is recognized that the solvent absorption/flash regeneration process is well suited for applications to separate refinery gas components into light and heavy products, typically hydrogen and methane, and to separate natural gas streams into light and heavy products, typically nitrogen and methane. This process would typically be located after the contaminant removal process.

In this embodiment the present invention provides incorporates surge capacity or capacitance for contaminants that are heavier than the light component into the absorption/flash regeneration process. This surge capacity allows the process to accommodate some short term contamination of the feed gas at levels above that acceptable in the product streams. According to one embodiment of the present invention surge volume provided in one or more of the process vessels in increased to above the minimum size required for the primary purpose of the process in order to hold some of the feed contaminant for a longer period of time before it is released into a product stream. According to another embodiment of the present invention, the solvent contains a portion of an external solvent that has characteristics that improve the system ability to absorb the contaminant, and in this manner hold at least some of the feed gas contaminant for a period of time before release into the product stream. It is counter-intuitive that a gas separation process that is operated as a steady-state continuous process can be adapted to pass through some short-term feed gas contaminant concentration spikes without having the product streams contaminated. However, in an absorption/flash regeneration process where all but the lightest components are first absorbed and then released from a solvent, the ability to tailor the solvent composition to hold a contaminant more readily combined with ability to set the volume of the solvent system can effectively dampen out feed gas contaminant spikes to the extent that product contamination may not occur.

The process of the present invention is applicable to any contaminant that can be absorbed by the solvent. If the solvent used is a simple physical solvent, with no special characteristics or affinities for selective absorption, the solvent will absorb at least a portion of any feed contaminant that is less volatile than the light component that is the extractor overhead product. The contaminant concentration will be reduced for the light product in this case. When the contaminant is less volatile than the primary heavy component, the contaminant concentration is reduced for both the light and the heavy products. The reduction of concentration in the heavy product is a transient until level of contaminant builds to a point that the contaminant is then released at the same rate at which it enters the system. In the case of a physical solvent, adding liquid surge volume to the system controls the amount of contaminant that can be accommodated without having the product stream contaminant concentration become too high. Additional capacitance can be added by utilizing a physical or chemical solvent that is selective for the anticipated contaminant. In this manner, addition of a small amount of a specialty solvent to the bulk solvent can greatly increase the system ability to dampen contamination spikes in the heavy product stream.

According to another aspect of the present invention, a chiller and separator are added to the heavy product stream, in a manner like that used for solvent recovery in prior art. Use of this recovery system can also help to reduce the amount of a contaminant that will leave with the heavy product stream in a given period of time.

The external solvent that is added to the process can be of any type. Exemplary solvents include paraffinic solvents, naphthenic solvents, iso-paraffinic solvents, and aromatic solvents. Solvents that are more specific for removal of the acid gas contaminants often associated with natural gas and refinery processing include sulfolane, selexol, morpholine and its derivatives, and a wide variety of compounds containing amine groups or glycol groups.

Characteristics of the solvent used can affect the purity of the produced product streams. If the light component is nitrogen separated from natural gas and preferably vented to the atmosphere, then contamination with even small amounts of propane and heavier hydrocarbons can exceed environmental regulations. If the light component is hydrogen separated from a refinery stream, then contamination with small amounts of components heavier than methane may reduce the hydrogen concentration and partial pressure to the extent that it is not usable for a desired refinery process. Propane or other components in the absorbed and released intermediate product stream may cause the intermediate steam to have an unacceptably high heating value or hydrocarbon dew-point.

The present invention removes contaminants from either or both the unabsorbed or the absorbed-and-released product streams. According to one aspect of the present invention, the contaminant could be removed prior to the primary absorption/flash regeneration process, but the contaminant is allowed into the process to increase efficiency by becoming part of the solvent and lowering the molecular weight of the solvent. According to another aspect of the present invention, the contaminant is then removed from either or both product streams that it contaminates. It is counterintuitive that a contaminant that can be removed from a feed stream, rather than from two product streams, should be left in the feed stream and allowed to contaminate the product streams. At times, the efficiency gained by leaving the contaminant in the feed to the main absorption process is so desirable that removal from two product streams is justified.

According to another aspect of the present invention, the contaminant is removed from the product streams using additional absorption/regeneration steps employing a solvent. The solvent used may be an internal solvent, an external solvent, or a combination of internal and external solvents. The absorbed component(s) may be released from the solvent using one or more flash vessels, using heat, using a distillation tower or stripping gas tower, or a combination of these standard, acceptable and proven methods. According to another aspect of the present invention, the contaminant is removed from the product streams using other established technologies including adsorption processes such as molecular sieves and silica gel, membrane separation processes, incineration, thermal oxidizer, and catalytic incinerator processes, and vapor/liquid separation at low temperatures achieved by any or all of expansion, heat exchange, and refrigeration. An intermediate boiling component can also be removed by stripping it from a slipstream of the circulating solvent in order to keep the concentration low enough that contamination of either the light or heavy product is reduced to acceptable levels.

Aspects of the present invention can be better understood with reference to the drawings and the following discussion of the embodiments depicted in the drawings. Where numbered components are not specifically discussed in the text, they can be assumed to have the same identity and purpose as the corresponding numbered component in the discussion of the previous or prior drawings.

FIG. 1 shows a prior art process without solvent inventory controls and that is non-specific regarding either external or internal solvent. According to the process of FIG. 1, hydrocarbon feed gas 1 is counter-currently contacted with lean solvent 2 in extractor 3, generating an overhead stream 18 and a rich solvent bottoms stream 4. The rich solvent bottoms stream 4 can is directed to one or more flash separators 5. The number of separators can vary. According to one embodiment, there is a single flash separator 5. The component absorbed in the solvent is released in separator 5, and is separated as vapor stream 6. While only one flash stage is depicted in FIG. 1, multiple separators could be used. The pressure of stream 6 is elevated via compressor 7, yielding stream 8 as a product stream of the process. The regenerated lean solvent leaves separator 5 as a liquid stream 9 and is returned to extractor 3 as stream 10 via pump 12. Lean solvent stream 10 may be cooled in solvent cooler 11 prior to re-entering the extractor 3. If the multi-component gas stream 1 entering the process of FIG. 1 comprises methane and nitrogen, for example, natural gas contaminated with nitrogen, then an external solvent would be utilized and stream 18 will be enriched with nitrogen and stream 8 will be enriched with methane. However, stream 8 is often contaminated with a significant amount of nitrogen because nitrogen co-absorbs with methane into the solvent. Ideally, contacting stream 1 with solvent would result in overhead stream 18 being nitrogen and stream 4 being solvent enriched only with absorbed methane. However, under real working conditions, feed composition and operating conditions result in an undesirable amount of nitrogen being co-absorbed into the solvent stream 4 along with the desired absorbed component, i.e., methane.

Figure 2:
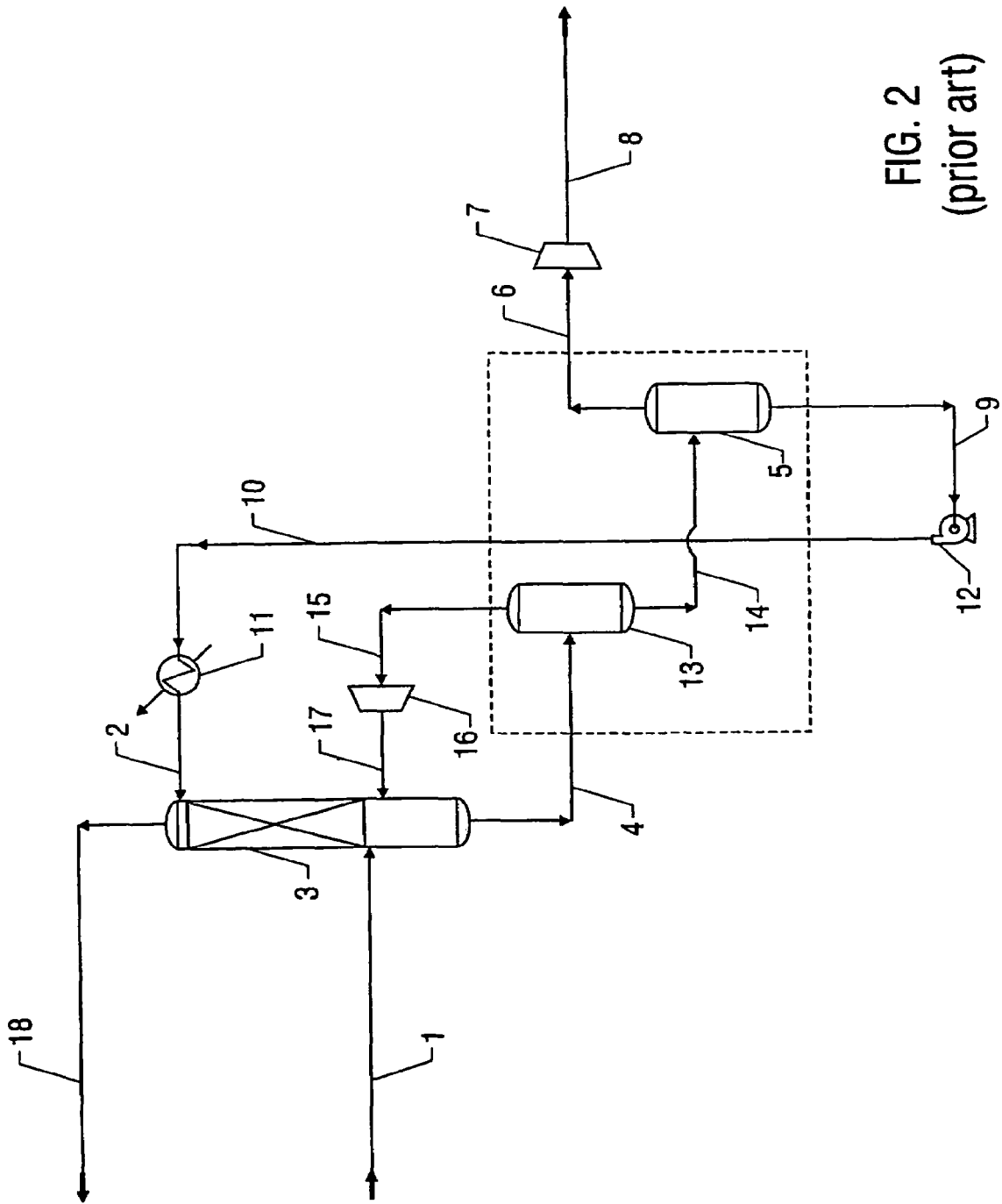
FIG. 2 shows a prior art process for separating the components of a gas wherein the process includes recycling a portion of the overhead gas stream from a flash separator back to the extractor.

FIG. 2 shows a prior art process that reduces the amount that the product stream is contaminated with co-adsorbed light components. The process of FIG. 2 utilizes two flash-regeneration separators, intermediate flash 13 and final flash 5. Overhead stream 15 from intermediate flash 13 is recompressed by recycle compressor 16 and recycled to extractor 3. Final flash 5 generally operates at a lower pressure than intermediate flash 13. Because nitrogen is a lighter component than methane, intermediate flash 13 preferentially releases the co-absorbed nitrogen and preferentially leaves the desired methane in the enriched solvent 14. Nitrogen rich gas stream 15 is recompressed and returned to extractor 3, preferably at a point in the extractor that is equal to or below the feed gas stream 1. This results in stream 18 being further enriched with nitrogen. Removing co-absorbed nitrogen from stream 4 results in final product stream 8 containing less nitrogen. The process according to FIG. 2 provides a higher purity product stream but requires an additional nitrogen compressor (16) and an additional flash stage (13). FIG. 2 is non-specific for use of external or internal solvent.

Figure 3:
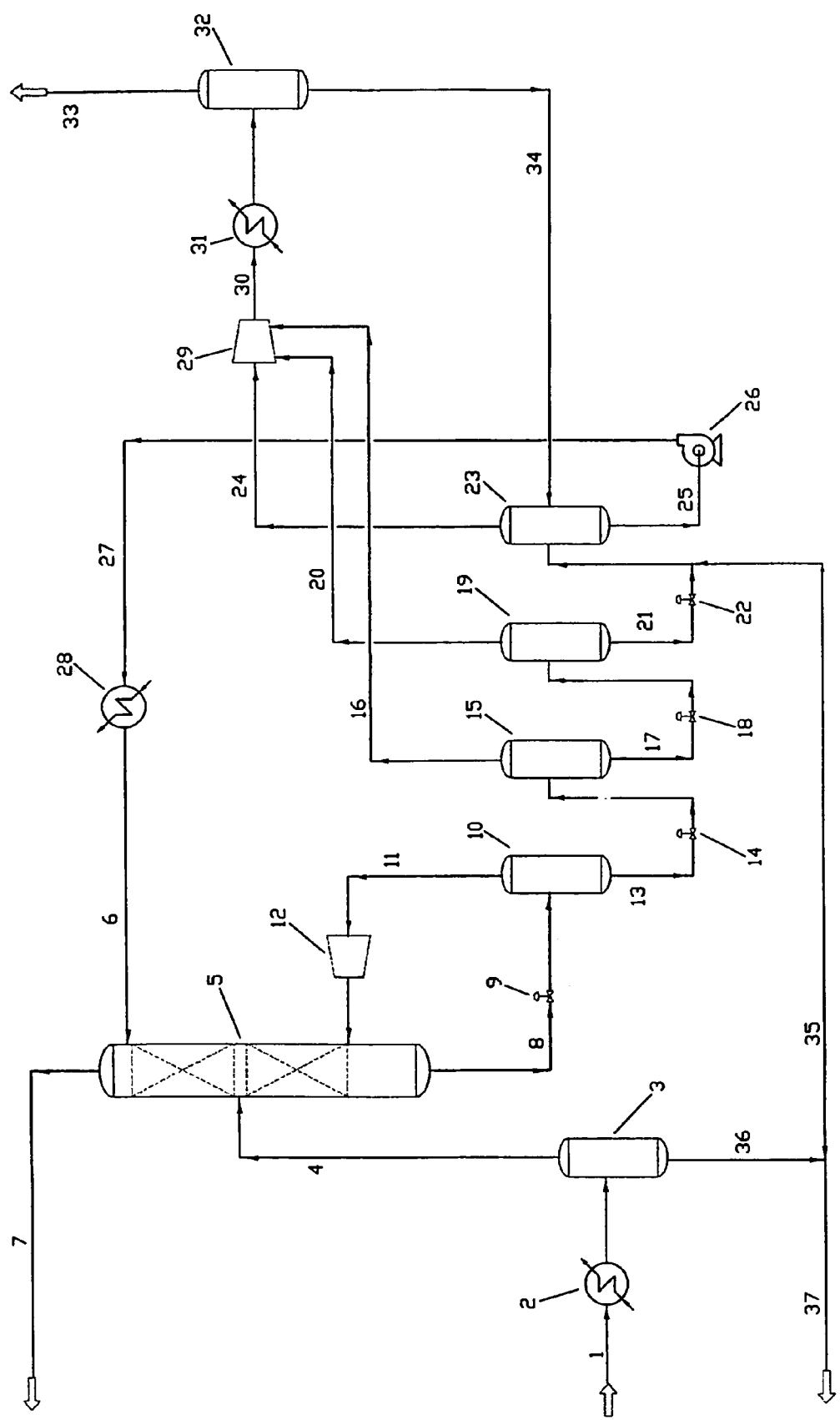
FIG. 3 shows a prior art process for separating the components of a gas stream wherein the process includes methods for internal solvent inventory control.

FIG. 3 depicts prior art that includes two points for solvent inventory control, and was developed for use with internal solvents. A multi-component gas stream 1 is cooled in chiller 2, and enters separator 3 where vapor and liquid phases are separated. The vapor phase is introduced to extractor 5, where the vapor is contacted with lean liquid solvent stream 6. The lean solvent absorbs intermediate and heavy components from the vapor, leaving the light components to exit the extractor top as vapor stream 7. The rich solvent, containing absorbed intermediate and heavy components, exits the bottom of the tower as stream 8 after being contacted with vapor recycled to the bottom of the extractor. Stream 8 is reduced in pressure by restrictor 9, and the resulting vapor and liquid phases are separated in separator 10. The vapor stream 11 contains a portion of the light component that was co-absorbed in the extractor, and this vapor is recycled via compressor 12 to re-enter the bottom of the extractor as a stripping gas. The rich solvent exiting the bottom of separator 10 as stream 13 contains the intermediate absorbed component(s) and absorbed heavy components. Sequential restrictors 14, 18, and 22, combined with sequential separators 15, 19, and 23 reduce the pressure of the rich solvent and separate the intermediate components from the circulating solvent containing heavy components. Vapor streams 16, 20, and 24 contain the intermediate components of the feed stream. Any number of flashes may actually be employed. Final separator liquid phase stream 25 is the lean solvent, with the majority of the intermediate components removed. The pressure of stream 25 is increased in pressure using pump 26 to become stream 27. Stream 27 is chilled in chiller 28 to become the lean solvent stream 6 that enters the extractor. The intermediate product streams 16, 20 and 24 are compressed in a multistage compressor 29 to become stream 30. This stream is chilled in chiller 31 and separated into a vapor and liquid phase in separator 32. The vapor portion exits the system as intermediate product stream 33. The liquid stream 34 contains solvent weight components that vaporized with the intermediate weight components in the flash vessels 15, 19, and 23, and were condensed by chilling at the elevated pressure of separator 32. These solvent components are re-introduced to the solvent system. If the temperature in separator 32 condenses more solvent component flow than is required to maintain the inventory of solvent in the system, then the excess solvent can be removed as a heavy product stream 35, and exit the system as stream 37. Stream 37 can be stabilized by removal of lighter components in a stripping distillation tower to meet heavy product specifications if desired. Conversely, if the temperature in separator 32 cannot recover enough heavy solvent components to maintain inventory of solvent, then condensed heavy components from separator 3, stream 36, may be added to the solvent inventory by flow in the opposite direction in FIG. 3. Control of the liquid from separators 3 and 32, along with control of the operating temperatures in these separators can be used to control inventory of internal solvent. Recovery methods can also be added to the light stream 7 to recover any heavy components contained in this stream, also.

Figure 4:
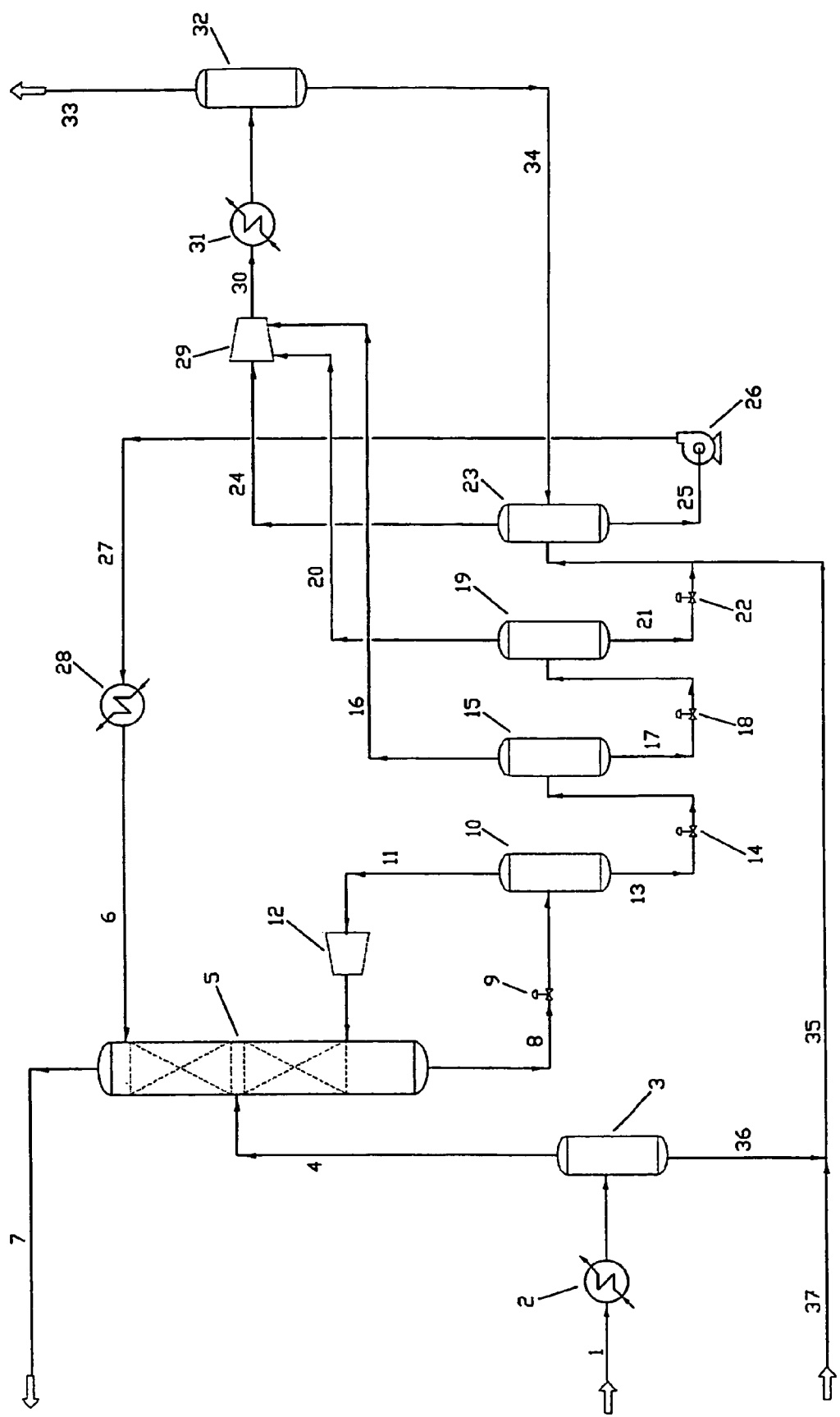
FIG. 4 shows a process according to the present invention for separating the components of a gas similar to the process of FIG. 3 but also providing for addition of external solvent component(s), and potentially eliminating one or more of the solvent inventory controls.

FIG. 4 depicts an embodiment of the present invention. Flow of stream 37 is reversed from FIG. 3. Stream 37 introduces external solvent to the system, to be used to augment internal solvent available and also to potentially reduce the need for solvent inventory recovery control points such as solvent recovery chiller and separator 31 and 32, or solvent recovery systems potentially employed on stream 7. FIG. 4 can also be used to depict the control embodiments of this invention. The solvent is continuously circulated through absorber 5 and flash vessels 10, 15, 19, and 23. Rate of solvent entering the absorber is a typical control point (valve not indicated). The level of solvent is kept in each vessel using a level measurement device (not indicated) and a level control valve (indicated as valves 9, 14, 18, and 22). An Example will be given to describe the -control and effects of control. FIG. 4 can also be used to describe the addition of selective solvent components using stream 37 to affect dampening of contaminant concentrations in the product streams, or the effect of vessel sizing and operating conditions on contaminant levels in product streams. An example will be given to describe this, also.

Figure 5:
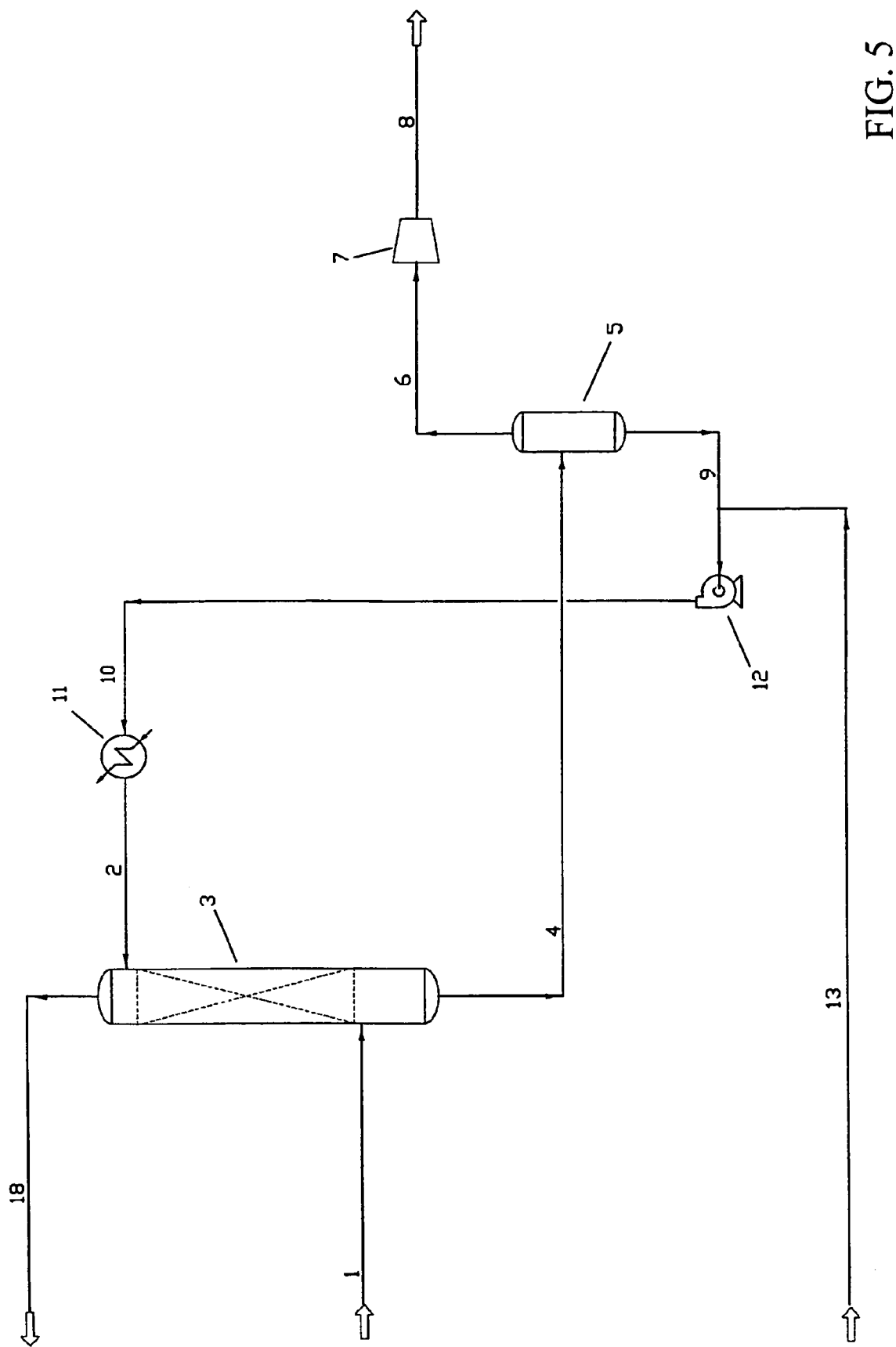
FIG. 5 shows a process according to the present invention in which addition of a portion of external solvent is added to the simple process of FIG. 1.

FIG. 5 depicts a most simple embodiment of the present invention. Stream 13 is a heavy solvent stream that can be added to a system like that of FIG. 1 that has some heavy components available for solvent from the feed gas, but not enough to maintain a solvent inventory without at least an initial external heavy solvent charge. Stream 13 may be added to process by insertion into stream 1, 2, 4, 9, or 10 and will in all cases become part of the lean solvent.

Figure 6:
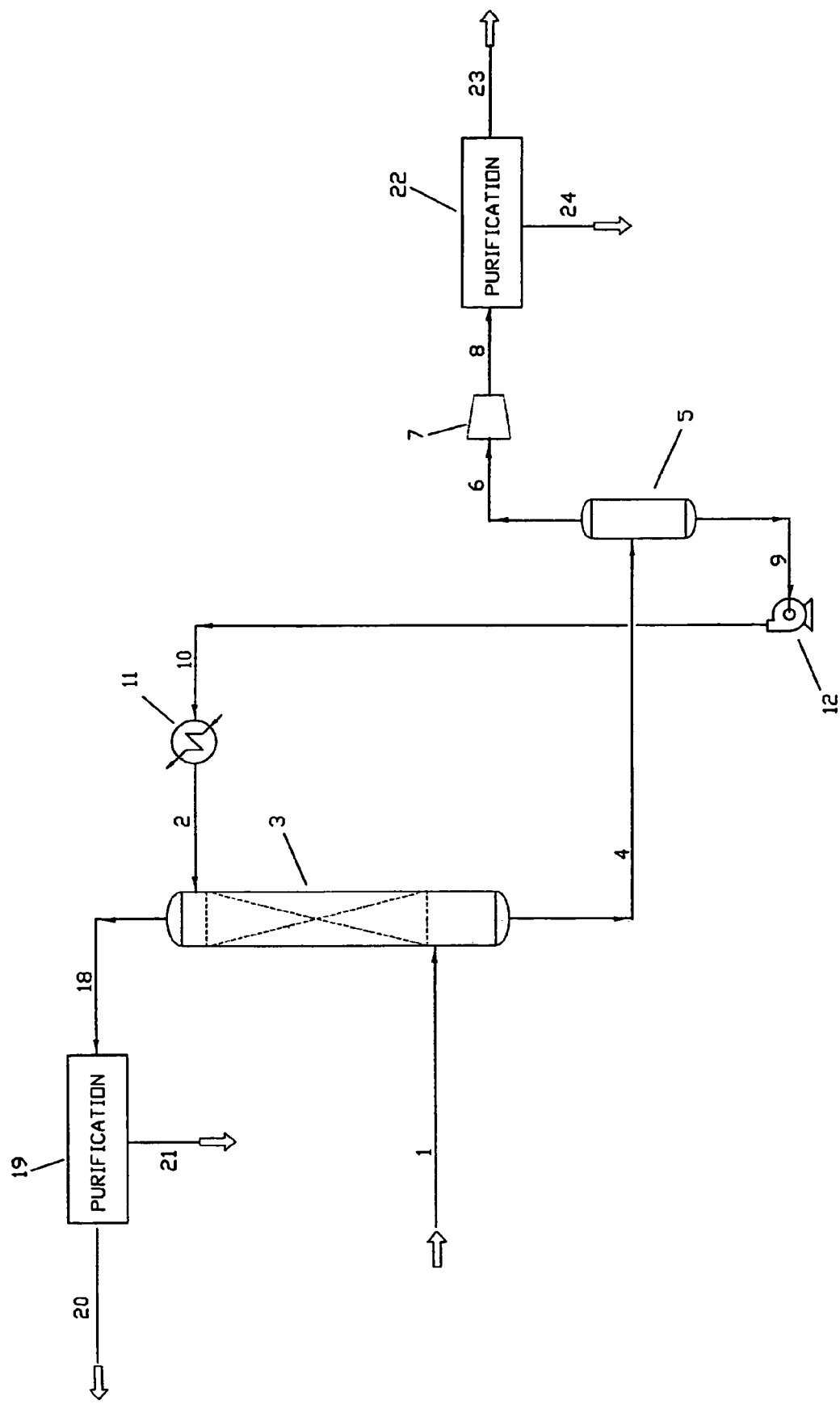
FIG. 6 shows a process according to the present invention for separating gas as in FIG. 1, with an additional purification step on one or more products indicated.

FIG. 6 depicts a most simple embodiment of the separated stream purification embodiment of the present invention. The process of FIG. 1 has additional product purification steps 19 and 22 added to the process, resulting in purified product streams 20 and 23 respectively, and removed contaminant streams 21 and 24 respectively. Either or both steps 19 and 22 may be utilized. Either or both steps 19 and 22 may be absorption, adsorption, membrane technology, or incineration technologies, or other technologies. Recovered streams 21 and 24 may be separate products as produced by their respective processes, or may be all or partially recycled into the main process.

Figure 7:
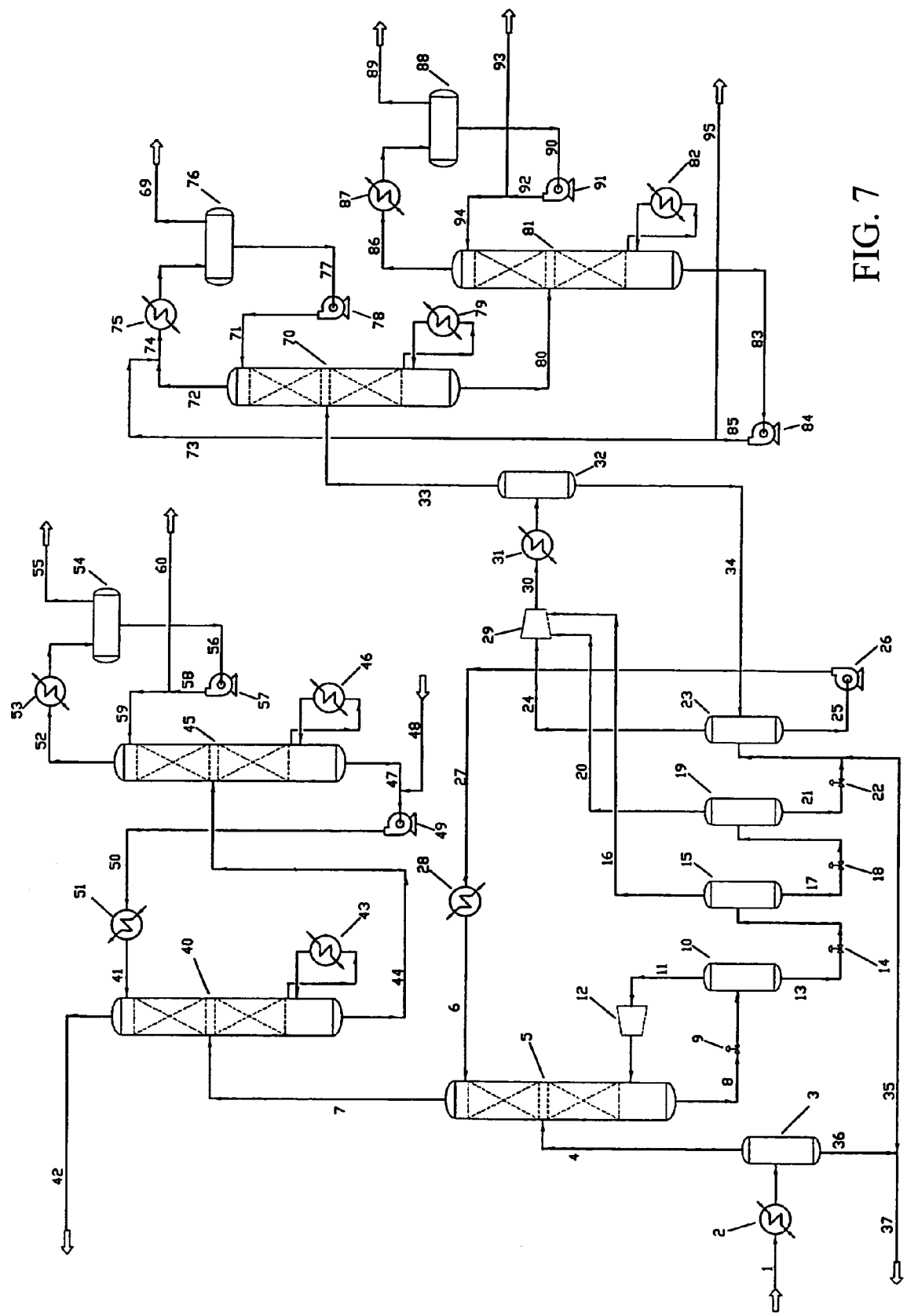
FIG. 7 shows a process according to the present invention according to FIG. 3 wherein the additional purification steps are absorption-based and are integrated into the main solvent absorption system.

FIG. 7 depicts an embodiment of the present invention utilizing absorption technology for purification of both product steams. The main process as depicted in FIG. 3, or FIG. 4 streams 1 through stream 33 is unchanged. An absorption regeneration process is depicted acting on the light, unabsorbed main process product stream 7 by items and streams numbers 40 through 60, resulting in purified light product stream 42. Stream 7 enters absorber 40, is contacted with lean solvent stream 41, and produces overhead product stream 42 that is leaner in one or more components than stream 7. Absorber 40 is equipped with reboiler 43 to control absorption of lightest components from stream 7. Rich solvent stream 44, containing desired absorbed components exits the absorber bottom, and is directed to regenerator tower 45. the absorbed component(s) are rejected from the solvent in tower 45 using the heat of reboiler 46, producing lean solvent stream 47 as the bottoms product stream. If solvent make-up is required, it may enter as stream 48, or conversely excess accumulated solvent may be removed at this point. Lean solvent is pumped by pump 49, exiting as stream 50, and is cooled and/or chilled by exchanger(s) 51 to become lean solvent stream 41. The regenerator tower 45 overhead stream 52 is cooled and at least partially condensed in exchanger 53, and the cooled stream enters separator/accumulator vessel 54. If an overhead vapor product on the absorbed component is produced, it is stream 55. If a liquid product is produced, it is stream 60. Liquid from vessel 54, stream 56, enters pump 57, exits as stream 58, and at least part of the stream 58 enters the top of the tower 45 as reflux. Heavy or intermediate product stream 33 is further purified by equipment and streams 70 through 95, producing purified product stream 69. In this example figure, the absorption/regeneration system includes a solvent presaturation step in order to depict one type of variation possible in absorption systems. Base process stream 33 enters absorber 70 and is contacted with presaturated lean solvent stream 71, producing overhead product stream 72, and after bottom reboiling from reboiler 79, rich solvent bottoms stream 80. The overhead product 72 is combined with lean solvent stream 73 to become two-phase stream 74 which is cooled in exchanger 75 and then enters separator 76. Purified product stream 69 is the vapor from separator 76 and this is feed stream 33 with one or more components removed from in by this purification step. The separator liquid, stream 77, enters pump 78, and exits as presaturated solvent steam 71. Rich solvent stream 80 is separated as in the light product purifier absorption regeneration system(items 45 through 60). For the heavy product purifier, corresponding items are numbers 81 through 94. Rich solvent steam 80 enters regenerator tower 81, reboiler 82 heats the bottom of the tower, creating bottoms lean oil stream 83, which is pumped by pump 84 to become stream 85. Any excess solvent is removed as stream 95, and remaining lean solvent is stream 73. The regenerator overhead stream 86 is cooled in exchanger 87 and at least part of the stream is condensed, and separated in vessel 88. Any vapor product is removed as stream 89. Liquid stream 90 is pumped by pump 91 to become higher pressure stream 92. Any liquid product is removed as stream 93, and remaining stream 94 is routed to the regenerator 81 as reflux. The regenerator for either product purifier may actually be operated at higher pressure than the corresponding absorber, in which case the lean solvent pump is not installed, and a rich solvent pump would be used instead. When external solvents are utilized for either purification step, the external solvent may be made up of paraffins, aromatics, naphthalenes, or specialty solvents including amines, morpholines, glycols, sulfinol, etc.

EXAMPLE 1

This Example compares the process of the present invention, as described in FIG. 4 with the prior art process described in FIG. 3 with regard to ability to process a gas stream comprising methane and nitrogen and heavier components by absorbing the methane away from the nitrogen in order to produce a methane stream that meets typical pipeline quality for inert content. The comparison is conducted under conditions such that a prior art process according to FIG. 3 utilizes an internal solvent made up of the heavier components of the feed stream, and solvent inventory is controlled by use of a chiller on the methane (intermediate) product for solvent recovery. The feed gas stream is quite lean for heavy components, and as such the stream 36 liquid in the feed gas separator 3 has no flow. The process of FIG. 3 is compared with the process of FIG. 4. The temperature and pressure of the extractor remain the same for both cases, as do the pressures of all flash vessels, and so on. The only change made is to eliminate the solvent recovery step indicated by chiller 31 and separator 32. Both systems produce essentially the same methane stream containing a reduced amount of nitrogen in order to meet typical pipeline specification. In other words, the process of the present invention achieves the same separation using a simpler process and fewer pieces of equipment than the process of FIG. 3.

The feed gas (stream 1) composition is a natural gas containing 15% molar nitrogen, 83.85% molar methane, 1.00% molar butane and 0.15% molar hexane and has a flow rate of 5.00 MMscfd (0.142 MMscmd), temperature of 100° F. (38° C.), and pressure of 620 psig (42.8 barg). The feed gas and the solvent are both chilled to −10° F. (−23° C.). The process of FIG. 3 requires chilling the methane-rich product gas to −2° F. (−19° C.) in order to maintain a solvent inventory of the heavy components in the feed gas. The lean solvent circulated is approximately 82% hexane and 18% butane. A pipeline quality gas containing 3% nitrogen is produced, and 98.5% of the valuable feed gas methane is recovered in the methane product stream.

The above case using FIG. 3 is now compared to using the process of FIG. 4. The same gas feed rate and composition is used. The solvent recovery system operating at −2° F. (−19° C.) is not used, eliminating several pieces of processing equipment. In order to maintain solvent inventory, 10 gallons/day (0.038 m3/day) of octane is added to the system. The resulting lean solvent is 40% octane, 45% hexane, and 15% butane. Purity and recovery of methane is the same as accomplished by FIG. 3. As the lean solvent in somewhat heavier due to octane components, the circulating pump horsepower increases from 248 to 289 horsepower (185 to 216 kW). This increase in pump horsepower, the removal of several pieces of equipment, and the requirement for 10 gal/day (0.038 m3/day) of octane are the total differences between the two operations. Use of the external/internal solvent approach serves to save on capital investment, simplify operation, and make the system more stable for compositional changes in the feed gas.

EXAMPLE 2

This Example describes and compares the control process of the present invention using FIG. 4 and compares it with a typical control with regard to ability to react to process perturbations in a system that processes a gas stream comprising at least two components that are separated using an absorption/flash regeneration solvent process. The feed gas and product gas flow and composition is identical for both control systems, as are all related pressures and temperatures under steady-state operating conditions. For both systems the level control loops are adjusted to respond to perturbations at the same speed, and it is assumed that this speed is a good choice as an optimum of speed versus stability. For both systems, it is assumed that the level-controlled flash vessels and the absorber bottoms level all normally contain approximately two minutes volume of the circulating solvent. In this example it is assumed that the level control loops comprising a level measurement device working with a level control valve are arranged where-in the level in a vessel such at the absorber 5 is controlled by the downstream level control valve 9 which controls flow out of the vessel, vessel 10 level is controlled by valve 14, and so on. The last flash vessel, 23, does not have a level control valve. It is a surge vessel. Using the process of FIG. 4, when the solvent rate is increased using a flow control loop on the lean solvent stream 6, as would be required if the feed gas rate to the facility were increased, each of the LCVs 9, 14, 18, and 22 will open in sequence as their respective controllers respond to increasing levels. If each controller takes one minute to respond with an appropriate increase in flow rate of solvent leaving the vessel, the total elapsed time for the change in solvent flow to reach the last flash, 23, will be 4 minutes. Flash 23 must be constructed with an adequate surge time so that when the largest design flow rate change is made, for example an initial startup of the system from a no-flow condition, or addition of a second parallel pump to the operation, that flash 23 does not have too low of a level for proper operation at any time. If flow rate were doubled to twice the design rate with 2 minutes of surge at normal design rates in vessel 23, flash 23 would have no liquid left in it by the time that the additional pumped liquid returns back to vessel 23 after passing through each vessel and its respective level control system. Alternatively, if each vessel level is controlled by an upstream level control valve, when solvent flow rate is increased, the level will drop in vessel 23, and the upstream control valve 22 would open to maintain level, and so on back to the absorber 5, which would be the surge vessel for liquid volume. The response time and vessel sizing requirements for liquid are identical to the first case. However, if a vessel close to the middle of the sequence of vessels is chosen as the surge (uncontrolled level) vessel by having absorber 5 level controlled by valve 9, vessel 10 level controlled by valve 14, vessel 15 without a level control valve, vessel 19 level controlled by valve 18, and vessel 23 level controlled by valve 22, again with 1 minute for each vessel LCV to respond, the total elapsed time for a solvent flow rate change to return to the surge vessel, in this case vessel 15, would be 2 minutes. The level controls work in two directions from the perturbation (solvent flow rate) simultaneously, cutting the total elapsed time in half.

It is not necessary to know the absolute response time per vessel, or the vessel surge time, for someone skilled in the art to recognize that the system using a surge vessel near the center of the series will allow for a faster overall system response. This faster response will allow better control of the facility, which can contribute to better product quality, fewer plant upsets and shutdowns, and possibly improved safety of operation. Fewer upsets in the liquid levels will contribute to better operation of all other associated plant control loops. The faster response can also be taken advantage of by reducing the surge time requirement for any or all of the vessels, thereby reducing the installed cost of a new facility. In an extreme case, changing an existing facility that has the control loops aligned in sequence with the surge at one end to have the vessel in the center assigned as the surge by reassigning level control valves may make an inoperable facility operable. Making use of the additional information available from installing flow meters on the liquid lines from each vessel that could allow rate adjustments based on anticipated requirements when the solvent circulation rate is changed would further reduce the response time, again allowing for better operation or smaller equipment that can perform as well as larger equipment would without the added indicators.

EXAMPLE 3

This Example presents information related to processing of natural gas for removal nitrogen, with potential for carbon dioxide, hydrogen sulfide, or mercaptan contamination. The feed gas typically contains only methane and heavier hydrocarbons and nitrogen. The absorption/flash regeneration process will separate the feed into a light component product containing primarily nitrogen, and a heavy component, containing primarily methane. In order to meet pipeline specifications, the amount of nitrogen will typically be less than 4 mole percent. An external physical solvent of commercial VM&P Naphtha is assumed to be used is conjunction with heavier components of the feed gas.

The feed gas composition is a natural gas containing 15% molar nitrogen and 85% molar methane and heavier, at a pressure of 950 psig (65.5 barg). The feed gas and the solvent are both chilled to −25° F. (−32° C.). In this example the process of FIG. 4 achieves a separation of the feed into a 90% purity nitrogen stream and a 97% purity methane and heavier stream. Solvent recovery exchanger 31 is not required, and stream 36 has no flow rate. Solvent make-up stream 37 is very low. In the conditions of the extractor 5, the average k-value of nitrogen is 9.5, and the average K-value of methane is 2.6. This variation in volatility allows the naphtha solvent to selectively absorb the methane. Co-absorbed nitrogen is recycled with compressor 12 after release in the first flash, vessel 10.

At extractor conditions, the k-value of carbon dioxide averages 0.75, and the k-value of hydrogen sulfide averages 0.25. Both of these contaminants is less volatile than methane, and as such would be absorbed into the solvent readily. They are both released less easily than the methane, and are therefore concentrated in the lean solvent to a higher degree than the methane. If a temporary spike of hydrogen sulfide or carbon dioxide enters the system, a portion of the contaminant is passed through with the primarily methane product, and a portion remains in the solvent. The portion that remains in the solvent will dissipate into the methane product over time. The contaminant peak level exiting the facility is lower than the peak level entering, and the impact of the contaminant is reduced. A higher portion of the hydrogen sulfide is held in the solvent because of the lower volatility.

If methane and heavier product specifications are 4 ppmv hydrogen sulfide and 2 mole % carbon dioxide, the present invention will allow the feed gas entering the facility to contain more than these levels of contamination in methane for a short period of time, as a portion of the contaminant will be held up in the solvent, and slowly released later. Allowing higher feed concentrations can have a large impact on plant operability by allowing a product stream to continue to flow for a period of time while an upstream treating facility is adjusted to return contaminant removal efficiency back to normal.

Addition of additional surge capacity in any vessel will add to the ability to be able to handle contaminants by increasing the amount of contaminant held. The highest volume benefit is achieved at the highest pressure, the extractor 5, where the volatility of the contaminants is lowest. Temporarily increasing the operating pressure of the lower pressure flashes will also delay the release of the contaminant into the methane product. Reducing the pressure of the last flash to less than atmospheric pressure, from 2 to 14 psia, will allow release of the maximum amount of any intermediate boiling component in the solvent, including components of the overhead produced product, that may contaminate the unabsorbed overhead product.

Addition of a selective solvent such as sulfinol or morpholine to the naphtha would further increase the solvent ability to hold the contaminants, further increasing either the time that contaminants can be in the feed or the concentration of contaminants in the feed before the product methane would be contaminated.

The above example is equally applicable to separation of hydrogen from methane when contaminants are present.

EXAMPLE 4

This Example compares the process of the present invention as described in FIG. 7 with the prior art process described in FIG. 3 with regard to their ability to process a gas stream comprising methane and nitrogen and heavier components by absorbing the methane away from the nitrogen in order to produce a methane stream that meets typical pipeline quality for inert content. The comparison is conducted under conditions such that a prior art process according to FIG. 3 utilizes nearly entirely an internal solvent made up of the heavier components of the feed stream, and solvent inventory is controlled by use of a product chiller 31 for solvent recovery. Condensed hydrocarbon liquid from the feed gas, stream 36, is routed to the absorber to maintain it as part of the solvent inventory make-up.

The feed gas characteristics used for this example are a flow rate of 10 MMscfd (0.28 MMscMd), pressure of 565 psig (39 barg), temperature of 100 deg. F (37.8° C.), and a composition of the following, in mole percent: nitrogen—23.48, methane—64.37, ethane—8.12, propane—2.28, i-butane—0.65, n-butane—0.59, i-pentane—0.21, n-pentane—0.18, n-hexane—0.07, n-heptane—0.05.

The process of FIG. 3 is operated with the feed chilled to −15 deg. F. (−26.1° C.) as stream 4 and 36, the lean solvent stream 6 also chilled to −15 F (−26.1° C.), the solvent recovery chiller 31 operated at a temperature of +14 deg F. (−10° C.) to maintain solvent inventory with no net make-up or loss, and a solvent circulation rate of about 742 gpm (2.81 m3/min). This results in a sales gas (stream 33) composition of containing only 3.2% nitrogen, easily within pipeline specification for nitrogen content, and a nitrogen vent stream (stream 7) that contains less than 10% methane and over 88% nitrogen. The solvent recovery system operates at about 450 psig (31.0 barg) in this example.

The results of operating at FIG. 3 may not meet all desired purity specifications. The vent stream is a very significant enrichment of nitrogen, and higher solvent circulation can increase the purification. However, use of the light internally generated solvent (about 71 molecular weight) leads to over 680 tons/year (616 tonnes/year) of propane and heavier content in the vent stream, which may well exceed environmental goals. The sales gas has met nitrogen content goals, but the gross heating value of the stream is 1150 btu/scf (10,235 kcal/m3). This is higher than some pipelines will accept.

Using the process of FIG. 7, the vent and sales gas can be purified. Conditions for the main process are not changed. The vent absorber/regenerator set is added to the process, and an octane molecular weight solvent is used to absorb the propane-plus hydrocarbons. With a lean solvent rate of less than 10 gpm (0.038 m3/min) at −15° F. (−26.1° C.), the nitrogen vent propane-plus is reduced from 685 tons/year (616 tonnes/year) to less than 20 tons/year (18 tonnes/yr). The regenerator operates at lower pressure and rejects the absorbed components from the rich solvent, recreating the lean solvent. The rejected overhead components may be recycled to the main process. The operating temperatures, pressures, and weight of the added solvent can be varied for specific cases. The presaturated absorption/regeneration system added to the sales gas reduces the btu content of the sales gas from 1150 to 1084 (10,235 to 9,648 kcal/m3), with a circulation rate of only 17 gpm (0.064 m3/min), with operation at −15 deg. F. (−26.1° C.) in the presaturator, and a high quality propane-plus liquid product stream is removed as stream 93. The solvent used is made up of components in the feed gas in this case. External solvents or a combination of internal and external solvents may be used. The pre-saturator and absorber system operates at about 435 psig (30 barg) in this example. The presaturator improves recovery, but is not required for achieving a reduction in the sales gas btu content. In this example, the propane-plus product is withdrawn from the system for sale. In practice, a portion may be recycled to the main process to aid in maintaining solvent inventory, if desired.

Installation of a system like the sales gas purification system to process the feed gas for propane-plus removal could accomplish the same nitrogen vent and sales gas purity when followed by the process of FIG. 3. However, the amount of propane-plus that would need to be removed is much higher in order to control the propane-plus in the vent, leading to a higher cost and higher utility requirements. With removal of the propane-plus from the feed, more external solvent must be purchased and added to the process of FIG. 3 as the solvent, and system utilities and cost increase due to having an overall heavier solvent. Use of the two added processes of FIG. 7 is actually preferable to installation of a single system upstream of FIG. 3.

At times when alternative processes to absorption are preferable for purification of the nitrogen vent and/or the sales gas stream, they may also be used with the same affect of having a more economical main separation process via FIG. 3, and using a process including processes such as membranes, molecular sieves, incinerators, or silica gels to meet final product requirements.

The above Example 4 can be equally applied to separation of hydrogen from methane, with the purity of the hydrogen product and/or methane product affected by a component in the feed gas, such as ethane, propane, carbon dioxide, hydrogen sulfide, and so on. Solvents chosen for the additional purification steps may be specifically targeted at the contaminants to be removed, such as use of a compound selective for removal of carbon dioxide or hydrogen sulfide.

All of the methods and apparatus disclosed herein can be made and executed without undue experimentation in light of the present disclosure. While the methods of this invention have been described in terms of specific embodiments, it will be apparent to those of skill in the art that variations may be applied to the methods and apparatus and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended provisional claims.

What is claimed is:

1. A process for separating the components of a multi-component gas stream, the process comprising:
contacting the multi-component gas stream with a lean solvent in an extractor to produce an overhead stream that is enriched in at least one unabsorbed component gas and a rich solvent bottoms stream that is enriched in at least one absorbed component gas;

flashing the rich solvent bottoms stream in at least one reduced pressure stage to regenerate lean solvent and to produce an overhead product stream that is enriched in at least one absorbed component gas, wherein the reduced pressure stage comprises two or more flash vessels of which at least one is a surge vessel and wherein level control instrumentation for the extractor and flash vessels is aligned such as to allow the surge vessel to be close to the middle of the sequence of vessels to improve control; and recycling the regenerated lean solvent to the extractor.

2. The process of claim 1, wherein the multi-component gas stream comprises at least one hydrocarbon.

3. The process of claim 1, wherein the multi-component gas stream comprises one or more components selected from the group consisting of hydrogen, nitrogen, helium, argon, methane, ethylene, ethane, heavier saturated and unsaturated hydrocarbons and mixtures thereof.

4. The process of claim 1, wherein the multi-component gas stream comprises natural gas, coal gas, refinery gas or gas from chemical plants.

5. The process of claim 1, wherein the unabsorbed component gas comprises nitrogen.

6. The process of claim 1, wherein the unabsorbed component gas comprises hydrogen.

7. The process of claim 1, wherein the product stream comprises methane.

8. The process of claim 1, wherein the lean solvent comprises one or more of the components of the multi-component gas stream.

9. The process of claim 1, wherein the external solvent is selected from the group consisting of paraffinic solvents, naphthenic solvents, aromatic solvents and specially mixed solvents.

10. The process of claim 1, wherein the extractor is a tower with internals to promote mass transfer.

11. The process of claim 1, wherein the multi-component gas stream is counter-currently contacted with the lean solvent.

12. The process of claim 1, wherein the lean solvent is chilled to a temperature as cold as $-40°$ F. ($-40°$ C.).

13. The process of claim 1, wherein the lean solvent is cooled to a temperature as cold as $-185°$ F. ($-121°$ C.).

14. The process of claim 1, wherein the level control instrumentation comprises valves.

15. The process of claim 1, wherein the level control instrumentation comprises hydraulic turbines.

16. The process of claim 1, wherein a volume of rich solvent retained in the flash vessel is included to allow temporary accumulation of a contaminant in the rich solvent thereby allowing a product vapor to remain below a required specification.

17. The process of claim 16, wherein additional solvent volume is added to increase ability to accommodate contaminants.

18. The process of claim 16, wherein the external solvent comprises a solvent chosen for its ability to selectively hold a contaminant in the solvent.

19. The process of claim 16, wherein the external solvent comprises sulfinol, selexol, an amine compound, a glycol compound, or a morpholine compound.

20. The process of claim 16, wherein the contaminant comprises carbon dioxide, hydrogen sulfide, mercaptans, oxygen, water, or carbon monoxide.

21. The process of claim 16, wherein the operating pressure of the flash vessels is increased to reduce vaporization of a contaminant.

22. The process of claim 1 further comprising a purification step to further purify the overhead unabsorbed component gas, the flashed overhead product stream, or both.

23. The process of claim 22, wherein an absorber/regeneration system employing a circulating solvent is used in the purification step.

24. The process of claim 22, wherein adsorption, membrane, incineration or other technologies are used in the purification step.

25. The process of claim 1, wherein the pressure of the last flash vessel is below atmospheric pressure.

26. The process of claim 1, wherein at least one reduced pressure stage is conducted at below atmospheric pressure.

27. The process of claim 1 for separating the components of a multi-component gas stream, wherein:

the step of contacting the multi-component gas stream with a lean solvent occurs at a temperature of about $-6.7°$ C. to about $-40°$ C. in an extractor to produce an overhead stream that is enriched in at least one unabsorbed component gas and a rich solvent bottoms stream that is enriched in at least one absorbed component gas;

flashing the rich solvent bottoms stream in at least one reduced pressure stage to regenerate lean solvent and to produce an overhead product stream that is enriched in at least one absorbed component gas, wherein the reduced pressure stage comprises two or more flash vessels of which at least one is a surge vessel and a wherein level control instrumentation for the extractor and flash vessels is aligned such as to allow the surge vessel to be close to the middle of the sequence of vessels;

recycling the regenerated lean solvent comprising absorbed heavy components that do not flash from the rich solvent to the extractor; and adding an external solvent to the regenerated lean solvent forming a circulating solvent stream that contains both external solvent and heavy components.

28. The process of claim 1 wherein the lean solvent is internal solvent or external solvent.

29. The process of claim 27, wherein a volume of rich solvent retained in the flash vessel is included to allow temporary accumulation of a contaminant in the rich solvent thereby allowing a product vapor to remain below a required specification.

30. The process of claim 29, wherein additional solvent volume is added to increase ability to accommodate contaminants.

31. The process of claim 1 further comprising a purification step to further purify the overhead unabsorbed component gas, the flashed overhead product stream, or both.

32. The process of claim 31, wherein an absorber/regeneration system employing a circulating solvent is used in the purification step.

* * * * *